(12) United States Patent
Weston et al.

(10) Patent No.: US 8,262,553 B2
(45) Date of Patent: Sep. 11, 2012

(54) OPHTHALMIC SURGICAL CONSOLE SYSTEM

(75) Inventors: David Weston, Newport Beach, CA (US); Roger D. Thomas, Tustin, CA (US); John C. Huculak, Mission Viejo, CA (US)

(73) Assignee: Novartis AG, Basel (CH)

( * ) Notice: Subject to any disclaimer, the term of this patent is extended or adjusted under 35 U.S.C. 154(b) by 1577 days.

(21) Appl. No.: 11/522,563

(22) Filed: Sep. 18, 2006

(65) Prior Publication Data

US 2008/0125761 A1 May 29, 2008

(51) Int. Cl.
*A61B 17/00* (2006.01)

(52) U.S. Cl. ............................................ 600/1; 312/209

(58) Field of Classification Search .............. 606/1, 4–6, 606/10, 166, 167
See application file for complete search history.

(56) References Cited

U.S. PATENT DOCUMENTS

| | | | |
|---|---|---|---|
| 4,437,677 A | 3/1984 | Ksayian | |
| 4,625,731 A | 12/1986 | Quedens et al. | |
| 4,836,486 A * | 6/1989 | Vossoughi et al. | 248/281.11 |
| 4,933,843 A * | 6/1990 | Scheller et al. | 604/22 |
| 5,028,746 A | 7/1991 | Petrich | |
| 5,177,616 A | 1/1993 | Riday | |
| 5,179,447 A | 1/1993 | Lain | |
| 5,455,766 A | 10/1995 | Scheller et al. | |
| 5,627,584 A | 5/1997 | Nishikori et al. | |
| 5,667,179 A | 9/1997 | Rosen | |
| 5,924,988 A | 7/1999 | Burris et al. | |
| 6,007,036 A | 12/1999 | Rosen | |
| 6,022,088 A | 2/2000 | Metzler | |
| 6,024,427 A | 2/2000 | Underwood et al. | |
| 6,102,476 A | 8/2000 | May et al. | |
| 6,145,926 A | 11/2000 | Lin | |
| 6,179,263 B1 | 1/2001 | Rosen et al. | |
| 6,220,658 B1 | 4/2001 | Lukawski et al. | |
| 6,447,451 B1 | 9/2002 | Wing et al. | |
| D467,001 S | 12/2002 | Buczek et al. | |
| 6,510,049 B2 | 1/2003 | Rosen | |
| 6,526,896 B2 | 3/2003 | Woronecki et al. | |
| 6,587,333 B2 | 7/2003 | Tseng et al. | |
| 6,736,360 B1 * | 5/2004 | Buczek | 248/276.1 |
| 7,044,568 B2 | 5/2006 | Olivera et al. | |
| 2003/0023164 A1 | 1/2003 | Eichelberger et al. | |
| 2004/0068208 A1 * | 4/2004 | Cimino et al. | 601/2 |
| 2005/0027397 A1 * | 2/2005 | Niemeyer | 700/245 |
| 2006/0020213 A1 * | 1/2006 | Whitman et al. | 600/478 |
| 2008/0004728 A1 * | 1/2008 | Essex et al. | 700/90 |

* cited by examiner

*Primary Examiner* — Ahmed Farah

(57) ABSTRACT

A ophthalmic surgical console system reduces kinking or flow restrictions in the tubing/cables attached to a ophthalmic surgical console by rotatably mounting the head of the surgical console to the base of the surgical console. The screen on which surgical parameter outputs are displayed and control inputs are made is attached to the ophthalmic surgical console using a movable adjustable arm.

7 Claims, 5 Drawing Sheets

OPHTHALMIC SURGICAL CONSOLE SYSTEM

FIELD

The present invention pertains to equipment used in eye surgery; more particularly the present invention pertains to a vitreoretinal surgical console system used in eye surgery.

BACKGROUND

During most eye surgeries, the patient is laid on a substantially horizontal surface. The eye surgeon often sits at the head of the patient looking down over the patient's forehead into the patient's eyes. The scrub nurse that typically assists the eye surgeon sits at one side of the patient's head.

The surgical console needed by the surgeon to perform delicate procedures involved in vitreoretinal surgery is typically positioned near the knees of the patient. The cables and fluid lines running from the surgical console to the various instruments and handpieces used by a vitreoretinal surgeon are draped over the patient. Typically, the actual draping of the cables and the fluid lines over the patient is done by a sterile nurse. The sterile nurse must take great care to keep the tubing sections as straight as possible to avoid kinking and to avoid constricting the range of movement of both the cables and the fluid lines. Such precautions are taken to not restrict the ability of the surgeon to move the instruments and hand pieces attached to the cables and fluid lines.

Prior art vitreoretinal surgical consoles used in various types of eye surgery typically include a screen or monitor which the scrub nurse uses to assist the physician by changing various parameters enabled by the surgical console. As the vitreoretinal surgical console is located near the knees of the patient, the screen or monitor is also located near the knees of the patient. Such location requires the scrub nurse to turn a full ninety degrees then adjust her vision from something up close to something a few feet away.

Accordingly, there is need for an ophthalmic surgical console system which avoids the kinking of the tubing and cables running from the equipment console to an eye surgeon and at the same time maximizes the usable service lengths of the tubing and cables for unrestrained movement by the eye surgeon. There is also an additional need in the art for providing better access to the input screen or monitor mounted on the ophthalmic surgical console.

SUMMARY

The ophthalmic surgical console system of the present invention avoids kinking of the cables and tubing running to the instruments and handpieces used by an eye surgeon and provides for unrestrained movement by the eye surgeon. In addition, the ophthalmic surgical console system of the present invention provides better access to the input screen for the scrub nurse.

The disclosed ophthalmic surgical console system is built to have a rotating and elevatable head. In addition, the input screen or monitor is mounted on an adjustable arm so that it may be moved to a position in close proximity to the scrub nurse.

By rotating the head on the ophthalmic surgical console system, the amount of bending in the cables and tubing is decreased thereby reducing the possibility of kinking of the cables and the tubing running from the console to the eye surgeon and increasing the range of unrestrained movement of the eye surgeon. Further, by moving the input screen to a location near the scrub nurse, quick, accurate inputs using the input screen are facilitated.

BRIEF DESCRIPTION OF THE DRAWING FIGURES

A still better understanding of the ophthalmic surgical console system of the present invention may be had from the following drawings when read together with the Description of Embodiments.

DESCRIPTION OF THE EMBODIMENTS

Figure 1:
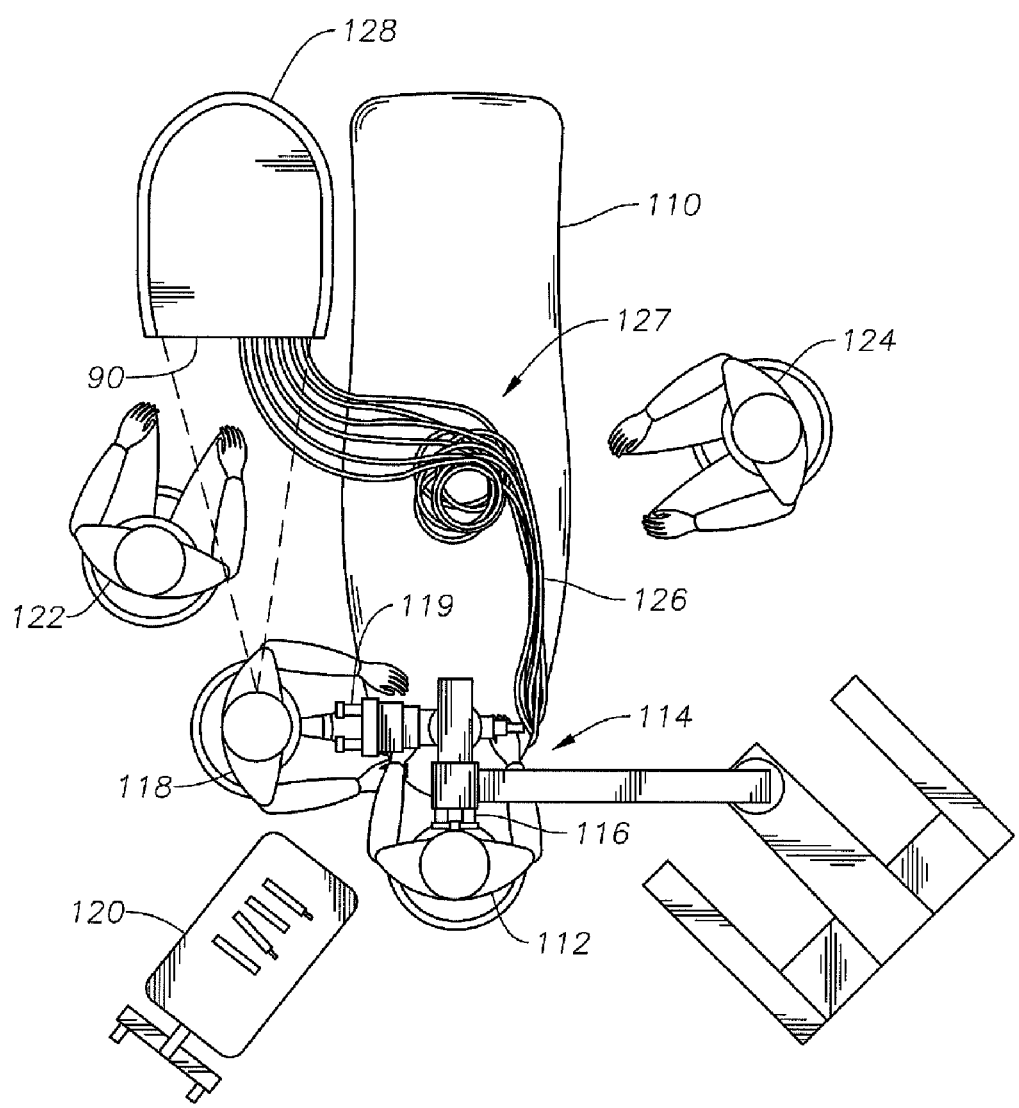
FIG. 1 is a plan view of a prior art ophthalmic surgical console system in an operating room setting showing its relationship to its users and an operating table.

Those of ordinary skill in the art will recognize the plan view of an operating room with a prior art vitreoretinal surgical console system shown in FIG. 1 in which eye surgery is typically performed. The patient is positioned to lie on an operating table 110. The surgeon 112 performing the eye surgery is positioned at the head 114 of the operating table 110 close to a pair of eye pieces 116 through which the operating field is observed. Seated next to the eye surgeon 112 is a scrub nurse 118, who has access to a second pair of eye pieces 119. Alternatively, a surgeon 112 who prefers to sit in the position shown by scrub nurse 118 in FIG. 1 can use eye pieces 119. Between the eye surgeon 112 and the scrub nurse 118 is a tray 120 on which instruments, handpieces, supplies and consumables are positioned. Also in the operating room may be a circulator 122 positioned near a surgical console 128 for providing the fluids, control inputs, and surgical parameter readouts needed during the surgery. Also in the operating room may be a second circulator 124.

Those who have used the array of equipment depicted in FIG. 1 have observed that it exhibits several drawbacks. Among those drawbacks are the difficulty experienced by the scrub nurse 118 in seeing the screen or monitor 90 on which sensor readouts are portrayed. Specifically, the scrub nurse 118 is required to turn about 90° in a counterclockwise manner to observe the screen or monitor 90 on which sensor readouts are portrayed. In addition, the screen or monitor 90 is more than half a body length away from the scrub nurse. Thus, a circulator may be needed if the screen is a GUI featuring touch-screen control inputs.

Another drawback of the array of equipment depicted in FIG. 1 is the tendency for the creation of flow restrictions in the tubing/cables 126 which pass over the patient from the console 128 to the surgeon. Because of the position of the surgeon 112 and the design of the console 128, the tubing/cables 126 are caused to bend at about a 90° angles. For some tubing, such a bend will restrict the amount of flow of a fluid capable of passing through the tubing. In addition, a service loop 127 is often required to give surgeon 112 the necessary ability to move the instruments and handpieces during surgery. Service loop 127 may increase the likelihood of kinking of tubing/cables 126.

Figure 2:
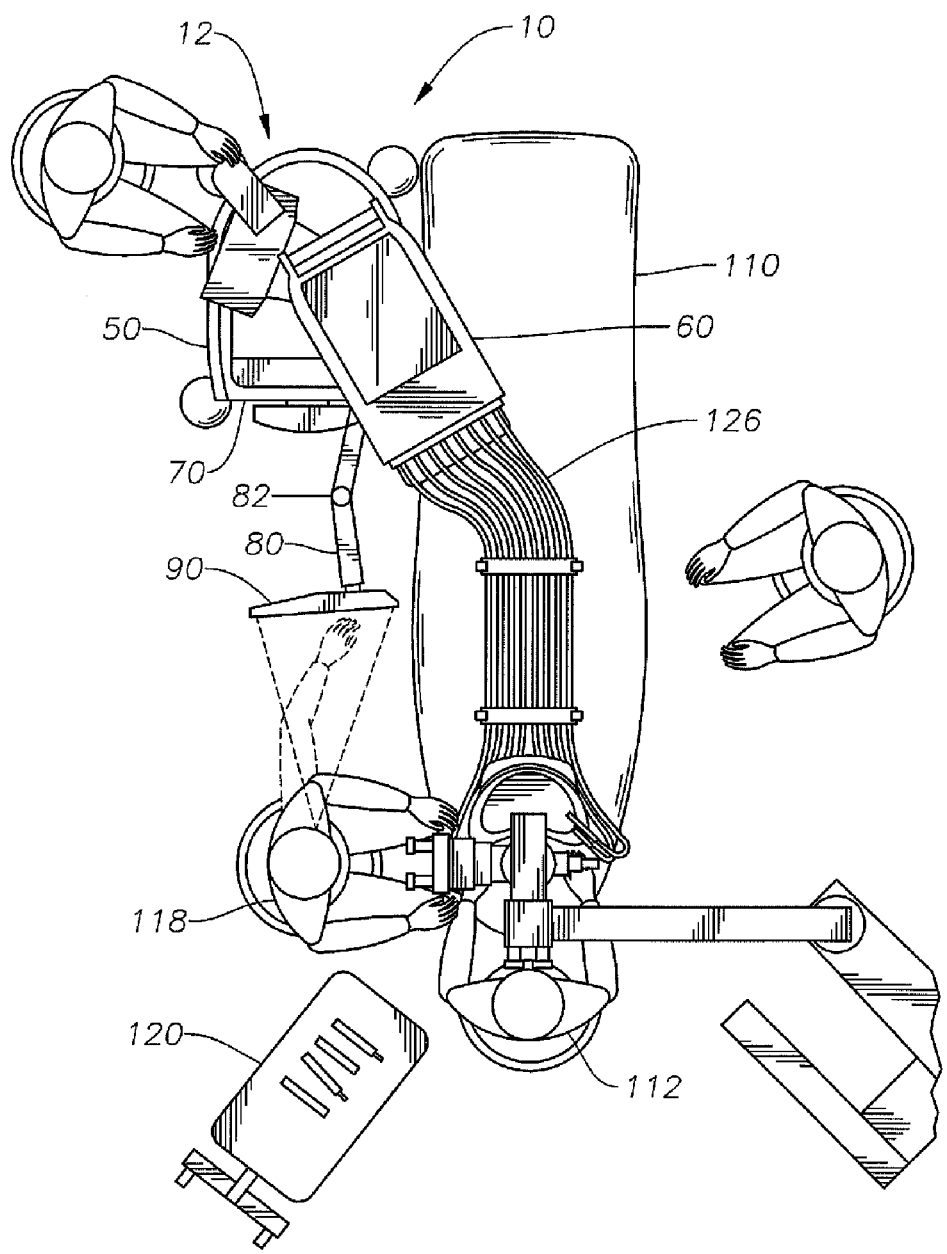
FIG. 2 is a plan view of the ophthalmic surgical console system of the present invention in relationship to its users and an operating table.

A plan view of an operating room using the disclosed ophthalmic surgical console system 10 is shown in FIG. 2. The disclosed system 10 is described herein in connection with a vitreoretinal surgical console 12. However, those of ordinary skill in the art will understand its applicability to other ophthalmic or other surgical consoles as well.

First, it may be observed that the screen or monitor 90 used by the scrub nurse 118 is mounted on an adjustable arm 80 having one or more joints 82 to be moved closer to the scrub nurse 118. Such repositioning of the screen by use of adjustable arm mounted to the top 70 of the console 12 makes the screen or monitor 90 easier to see and allows the scrub nurse 118 to make touch inputs if a GUI touch-screen system is being used.

Second, it may be observed that the head portion 60 on top of the console 12 is now made to be rotatable with respect to the base or body portion 50 of the console. The impact of allowing the head 60 of the machine to rotate with respect to the body 50 has a significant effect on the bending of the tubing/cables 126. A comparison of FIG. 1 to FIG. 2 will reveal that the bending of the tubing/cables 126 has been reduced to about 15°. In yet another embodiment the head 60 may be mounted to the body on a vertical movement mechanism so that it may move up and down as shown by arrow A in FIG. 3A and FIG. 3B. Such rotating and vertical movement mechanisms are well known to those of ordinary skill in the art.

Figure 3A:
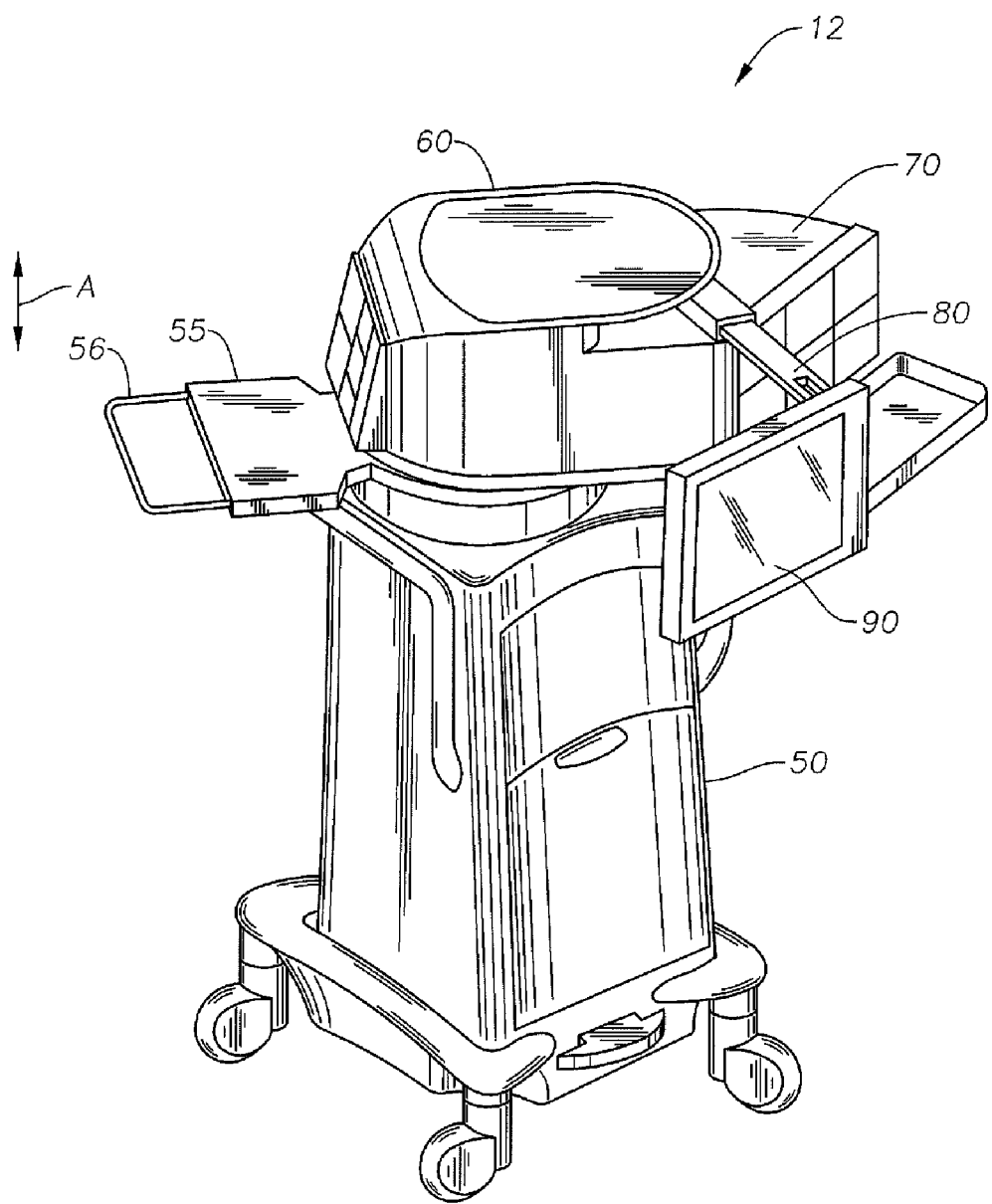
FIG. 3A is a perspective of the front of the ophthalmic surgical console system of the present invention.

A still better understanding of the present invention 10 may be had by reference to FIG. 3A which is a view of the machine generally from the perspective of the surgeon 112 and the scrub nurse 118. The screen or monitor 90 is located on an adjustable arm 80 and may be moved to where it is easily accessible by the scrub nurse 118. The head 60 of the console 12 is rotatably and elevatably mounted to the body 50 as explained above. Also included is a fold down work surface 55 with a wire loop 56 for holding a trash bag (not shown).

Figure 3B:
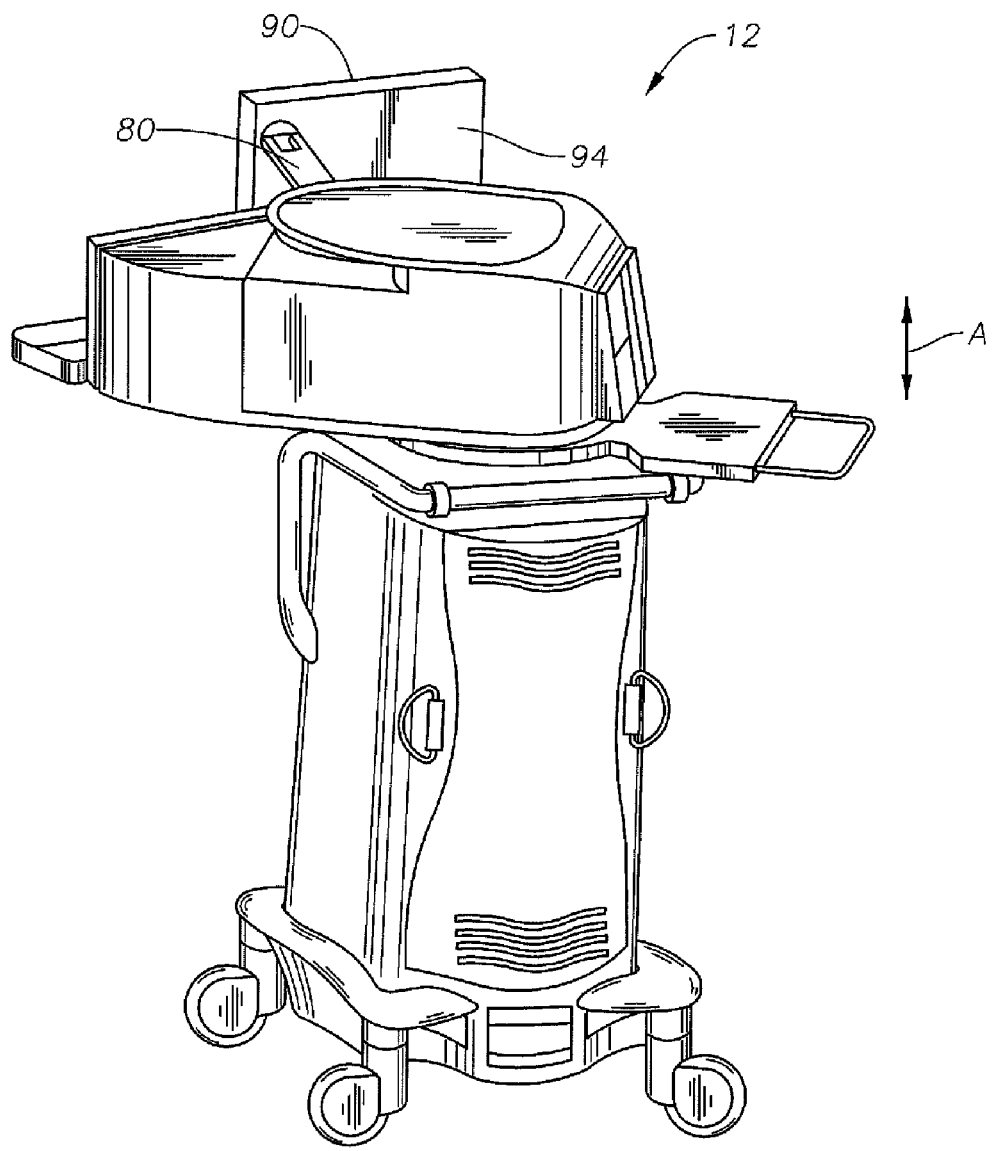
FIG. 3B is a perspective view of the back of the ophthalmic surgical console system.

FIG. 3B is a perspective view of the machine looking toward the eye surgeon 112 and the scrub nurse 118. In this view the back 94 of the screen or monitor 90 is shown along with its mounting to the adjustable movable arm 80. The rotability of the head 60 of the console 12 with respect to the body 50 of the console may also be observed.

Figure 4:
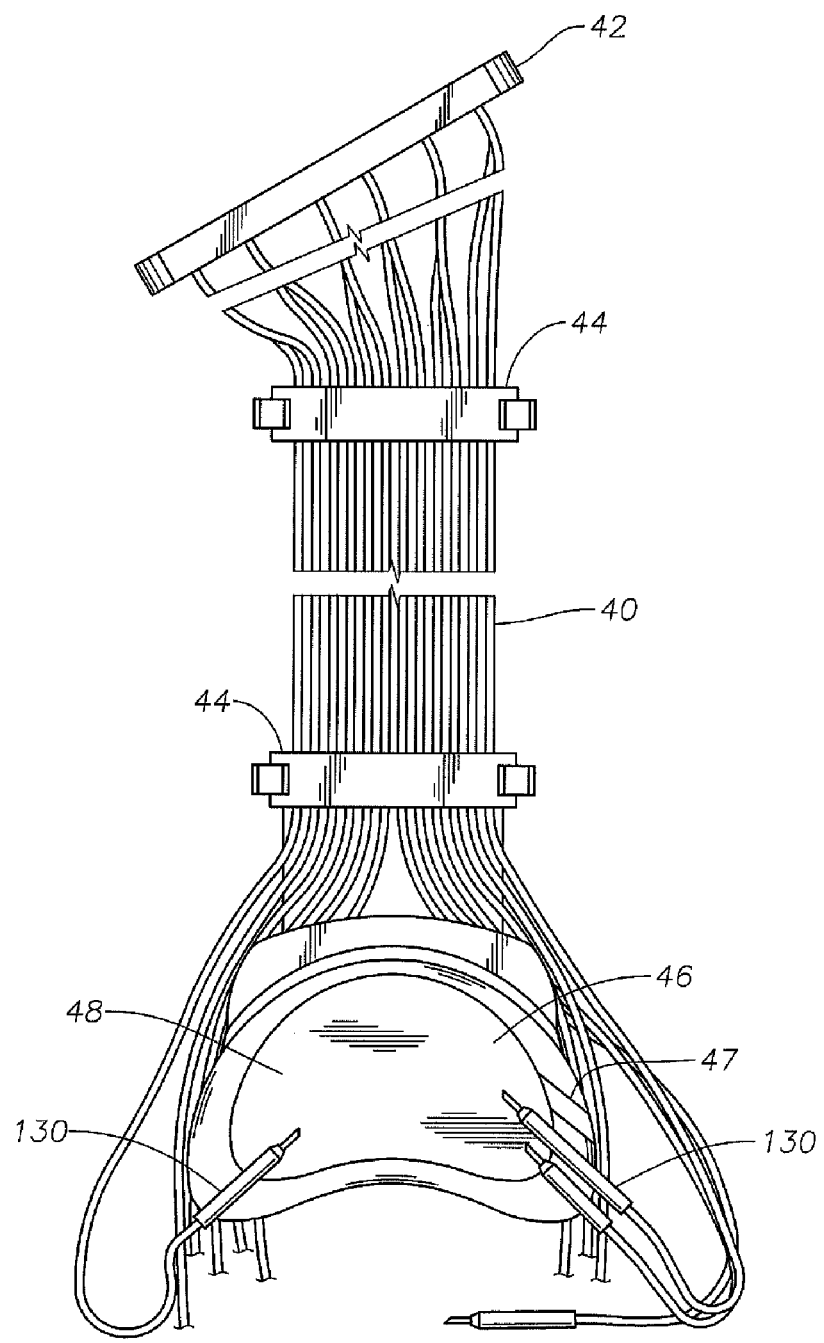
FIG. 4 is a plan view of one type of tubing/cable management system usable with the ophthalmic surgical console system of the present invention.

By making the head 60 of the console 12 rotatable and elevatable with respect to the body 50 of the console, a variety of different surgical procedures are enabled. Each one of these procedures is enabled by an array or a set 40 of tubing/cables connected to the various instruments and handpieces used during the surgery. An exemplary array or set of tubing/cables 40 along with associated mounting and alignment hardware appears in FIG. 4. The connection to the console 12 is made by use of a manifold 42 constructed and arranged for mounting to the rotating head 60. Alignment combs 44 are used to keep individual tubing/cables separate as they pass over the patient. At the opposite end of the tubing/cable assembly is a disposable tray 46 which includes receptacles 47 for holding the various instruments and handpieces 130 connected to the end of individual tubing/cables. Located on the bottom of the tray 46 or its supporting structure may be fold down stabilizers to provide greater support for the tray 46. Tray 46 may also have a dish 48 for holding surgical fluid for priming instruments and handpieces 130.

In an alternate embodiment, a circular rotatable lazy-susan type tray 46 may be placed at the end of the set of tubing/cables 40 when multiple instruments are required during a particular procedure. The array of instruments may be placed in slots on the rotatable tray and connected to individual tubing/cables as needed.

In yet another embodiment the set of tubing/cables 40 may be divided into two or more subsets where each subset is attached to another piece of equipment used during a particular procedure.

While the present invention has been disclosed according to its preferred embodiment, those of ordinary skill in the art will understand that still other embodiments of the disclosed invention has been enabled by the foregoing disclosure.

What is claimed is:

1. An ophthalmic surgical console system comprising:
   an array of tubing and cables connected to instruments needed for the performance of a procedure enabled by the ophthalmic surgical console, said array of tubing and cables connected to a manifold;
   a console base portion;
   a console head portion, said console head portion constructed and arranged to be rotatable with respect to said console base portion;
   said console head portion connected to said manifold;
   a movable, adjustable screen mounting arm connected to said head portion, said movable adjustable screen mounting arm constructed and arranged to position a screen near those performing the surgery using the ophthalmic surgical console.

2. The ophthalmic surgical console system as defined in claim 1 wherein said array of tubing and cables includes at least one cable/tubing alignment device.

3. The ophthalmic surgical console system as defined in claim 1 wherein said array of tubing and cables further includes a tray positioned at the opposite end of said array of tubing and cables from said manifold.

4. The ophthalmic surgical console system as defined in claim 3 wherein said tray further includes receptacles for instruments attached to said array of tubing and cables.

5. The ophthalmic surgical console system of claim 4 wherein said tray comprises a dish for holding surgical fluid for priming the instruments.

6. The ophthalmic surgical console system of claim 1 wherein said console head portion is constructed and arranged to be elevatable with respect to said console base portion.

7. The ophthalmic surgical console system as defined in claim 1 wherein said movable adjustable arm includes one or more joints providing for rotation about a substantially vertical axis.

\* \* \* \* \*